(12) United States Patent
Sayani et al.

(10) Patent No.: US 11,559,234 B2
(45) Date of Patent: Jan. 24, 2023

(54) PORTABLE ELECTROCARDIOGRAPHY DEVICE

(71) Applicant: The Aga Khan University, Karachi (PK)

(72) Inventors: Saleem Sayani, Karachi (PK); Muhammad Abdul Muqeet, Karachi (PK); Hafiz Imtiaz Ahmed, Karachi (PK); Hafsa Talat, Karachi (PK); Ayeesha Kamran Kamal, Karachi (PK); Ambreen Amir Ali, Karachi (PK); Naeem Sheikh, Karachi (PK)

(73) Assignee: The Aga Khan University, Karachi (PK)

( * ) Notice: Subject to any disclaimer, the term of this patent is extended or adjusted under 35 U.S.C. 154(b) by 1084 days.

(21) Appl. No.: 16/212,057

(22) Filed: Dec. 6, 2018

(65) Prior Publication Data

US 2020/0077917 A1 Mar. 12, 2020

(30) Foreign Application Priority Data

Sep. 6, 2018 (PK) .................................. 615/2018

(51) Int. Cl.
*A61B 5/282* (2021.01)
*G16H 50/50* (2018.01)
(Continued)

(52) U.S. Cl.
CPC ............ *A61B 5/282* (2021.01); *A61B 5/0006* (2013.01); *A61B 5/0022* (2013.01); *A61B 5/316* (2021.01); *A61B 5/339* (2021.01); *G16H 40/63* (2018.01); *G16H 50/50* (2018.01); *H02J 7/00* (2013.01); *H04M 1/72412* (2021.01); *A61B 2560/0456* (2013.01); *A61B 2562/0215* (2017.08); *A61B 2562/043* (2013.01); *A61B 2562/164* (2013.01); *A61B 2562/227* (2013.01); *G06F 3/14* (2013.01)

(58) Field of Classification Search
CPC .... A61B 2560/0456; A61B 2562/0215; A61B 2562/043; A61B 2562/164; A61B 2562/227; A61B 5/0006; A61B 5/0022; A61B 5/282; A61B 5/30; A61B 5/316; A61B 5/332; A61B 5/335; A61B 5/339; A61B 5/6898; G06F 3/14; G09G 2380/08; G16H 40/63; G16H 40/67; G16H 50/50; H02J 7/00; H04M 1/72412
See application file for complete search history.

(56) References Cited

U.S. PATENT DOCUMENTS 8,046,059 B2 10/2011 Cho et al.
8,509,882 B2 8/2013 Albert et al.
(Continued)

*Primary Examiner* — George Manuel
(74) *Attorney, Agent, or Firm* — Fish & Richardson P.C.

(57) ABSTRACT

An electrocardiography device is described that can include a main body, an adjustable cap, and a power switch. The main body can include an electrode of a plurality of electrodes configured to acquire electrical signal from a patient. The adjustable cap can include two electrodes of the plurality of electrodes. The adjustable cap can be rotatable around an axis on the main body to orient the plurality of electrodes on different locations on a body of the patient. The power switch can activate the plurality of electrodes to acquire the electrical signal from the patient. Related apparatuses, systems, methods, techniques and articles are also described.

20 Claims, 9 Drawing Sheets

(51) Int. Cl.
*G16H 40/63* (2018.01)
*A61B 5/00* (2006.01)
*H02J 7/00* (2006.01)
*A61B 5/316* (2021.01)
*A61B 5/339* (2021.01)
*H04M 1/72412* (2021.01)
*G06F 3/14* (2006.01)

(56) References Cited

U.S. PATENT DOCUMENTS

| | | |
|---|---|---|
| 8,855,757 B2 | 10/2014 | Kapoor |
| 9,026,202 B2 | 5/2015 | Albert |
| 2007/0184682 A1* | 8/2007 | Gobron .................. H01R 35/04 439/67 |
| 2011/0270112 A1 | 11/2011 | Manera et al. |
| 2013/0080836 A1* | 3/2013 | Stergiou ................ G16H 40/67 714/E11.178 |
| 2016/0213263 A1* | 7/2016 | Felix .................... A61B 5/4809 |
| 2016/0296132 A1 | 10/2016 | Bojovic et al. |

* cited by examiner

PORTABLE ELECTROCARDIOGRAPHY DEVICE

RELATED APPLICATION

This disclosure claims priority to Pakistan Patent Application No. 615/2018, filed on Sep. 6, 2018, and entitled "Portable Electrocardiography Device", the entire contents of which are hereby fully incorporated by reference.

TECHNICAL FIELD

The subject matter described herein relates to a portable electrocardiography device that can be configured to be an accessory of a mobile phone.

BACKGROUND

Cardiovascular diseases are one of the main reasons for human deaths throughout the world. For example, more than 17.5 million people die each year from cardiovascular diseases, and 80% of these deaths are caused due to heart attack and stroke. People often mistake cardiac symptoms for heart burn or panic attack, as the symptoms of a cardiovascular disease as well as heart burn and panic attack may be similar, such as chest pain, arm pain, neck pain, jaw pain, shortness of breath, cold sweats, and unexplained fatigue. To distinguish cardiovascular diseases from a heart attack or panic attack, doctors often perform an electrocardiogram to detect the electrical activity of the heart of a patient. Traditional electrocardiography devices are bulky and located at clinics or hospitals. For many patients, however, going to a clinic repeatedly for an electrocardiogram may be not only inconvenient but also challenging. Therefore, there exists a need for an electrocardiography device that is portable, is light in weight, is easy to use, and enables communication with an application that can display a diagnosis of the heart of the patient and permit the patient to remotely communicate with a clinician.

SUMMARY

In one aspect, an electrocardiography device is described that can include a main body, an adjustable cap, and a power switch. The main body can include an electrode of a plurality of (e.g., three) electrodes configured to acquire electrical signal from a patient. An electrode of the three electrodes can be fixed on the main body. The adjustable cap can include two electrodes of the plurality of electrodes. The adjustable cap can be rotatable around an axis on the main body to orient the plurality of electrodes on different locations on a body of the patient. The power switch can activate the plurality of electrodes to acquire the electrical signal from the patient.

In some variations, one or more of the following can be implemented either individually or in any suitable combination. The main body can further include an electrical circuit and a rechargeable battery. The electrical circuit can include a communication receiver, one or more electronic amplifiers, one or more electronic filters, an analog to digital converter, and a transmitter. The communication receiver can receive the acquired electrical signal from the plurality of electrodes. The one or more electronic amplifiers can amplify the received electrical signal. The one or more electronic amplifiers can include a pre-amplifier and an instrumentation amplifier. The one or more electronic filters can filter the amplified electrical signal. The one or more electronic filters can include a notch filter. The analog to digital converter can extract samples at discrete points in time of the filtered electrical signal. The transmitter can transmit the samples to an application executed on a mobile device. The rechargeable battery can power the electrical circuit. The electrocardiography device can further include a charging port configured to charge the rechargeable battery. The charging port can be a microUSB port. The electrodes can be made of at least one of silver and silver chloride. The electrodes can be leadless. The main body can be made of thermoplastic polyurethane.

In another aspect, a system can include an electrocardiography device and a mobile device. The electrocardiography device can receive an electrical signal from a body of a patient, and process the electrical signal into a digital electrical signal. The mobile device can execute an application. The application can receive, via a first communication network, the digital electrical signal from the electrocardiography device. The application can retrieve, via a second communication network, a predictive model from a computing server. The application can apply the predictive model on the digital electrical signal to predict a diagnosis for the patient. The application can display the diagnosis on a first graphical user interface of the application.

In some variations, one or more of the following can be implemented either individually or in any suitable combination. The application can construct a PQRST complex based on the digital electrical signal. The application can display the PQRST complex on a second graphical user interface of the application. The computing server can be a cloud computing server. The cloud computing server can include: a normalization processor configured to receive the digital electrical signal from the electrocardiography device; at least one of one or more software development kits and one or more web modules configured to facilitate communication with the mobile device; an application programming interface configured to facilitate communication between one or more processors and the mobile device; one or more controllers including the one or more processors; and one or more databases communicatively coupled to the one or more controllers.

In yet another aspect, a plurality of electrodes of an electrocardiography device can acquire an electrical signal from a patient. A communication receiver of the electrocardiography device can receive the acquired electrical signal from the plurality of electrodes. One or more electronic amplifiers within the electrocardiography device can amplify the received electrical signal. One or more electronic filters of the electrocardiography device can filter the amplified electrical signal. An analog to digital converter of the electrocardiography device can extract samples at discrete points in time of the filtered electrical signal. A transmitter of the electrocardiography device can transmit the samples to an application executed on a mobile device.

In some variations, one or more of the following can be implemented either individually or in any suitable combination. The electrocardiography device can include an adjustable cap including two electrodes of the plurality of electrodes. The adjustable cap can be rotated around an axis on the main body to orient the plurality of electrodes on different locations on a body of the patient. The electrocardiography device can include a power switch. The power switch can activate the plurality of electrodes to acquire the electrical signal from the patient. The mobile device performs operations including: receiving, via a first communication network, the samples from the electrocardiography device; retrieving, via a second communication network, a predictive model from a computing server; applying the predictive model on the samples to predict a diagnosis for the patient; and displaying the diagnosis on a first graphical user interface of the application.

The subject matter described herein provides many advantages. For example, the electrocardiography device is portable, is light in weight, is easy to use, and enables communication with an application that can display a diagnosis of the heart of the patient and permit the patient to remotely communicate with a clinician. Additionally, the electrocardiography device can have a simple structure/construction, as a result of which training on and troubleshooting of the device can be easy and quick, and can be performed by even a layman.

The details of one or more variations of the subject matter described herein are set forth in the accompanying drawings and the description below. Other features and advantages of the subject matter described herein will be apparent from the description, the drawings, and the claims.

BRIEF DESCRIPTION OF DRAWINGS

Like reference symbols in the various drawings indicate like elements.

DETAILED DESCRIPTION

Figure 1:
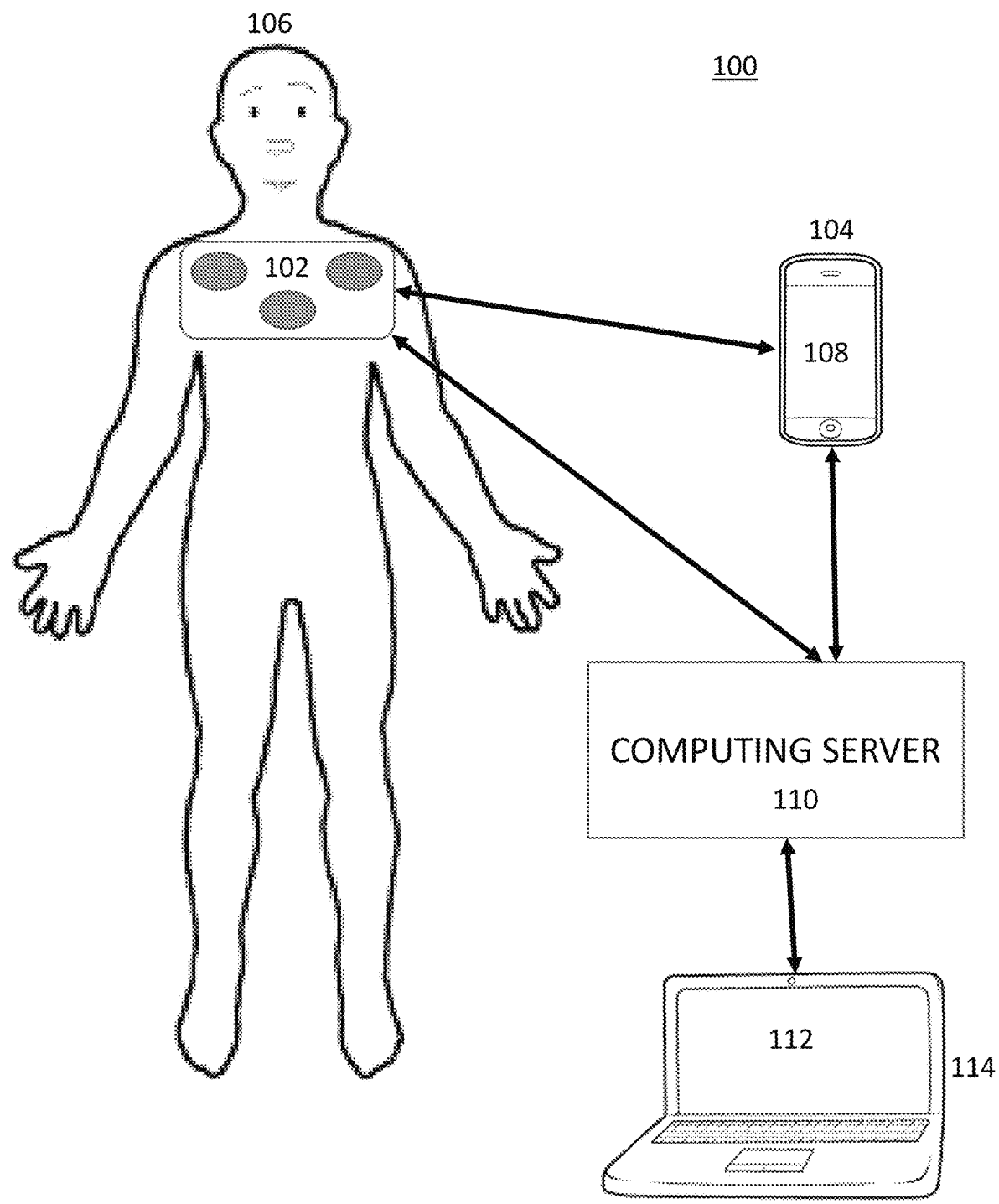
FIG. 1 illustrates a computing landscape in which an electrocardiography device can be used in conjunction with a mobile device.

FIG. 1 illustrates a computing landscape 100 in which an electrocardiography device 102 can be used in conjunction with a mobile device 104. The electrocardiography device 102 can be an accessory of the mobile device 104, and can be configured to be attached to a case of the mobile device 104 so that a patient 106 can perform electrocardiography on his body at his or her convenience or need, and a patient-application 108 on mobile device 104 can display a diagnosis specific to that electrocardiography. The patient-application 108 can be hosted by a computing server 110. In a first implementation, the patient-application 108 can generate the diagnosis. In a second implementation, the computing server 110, instead of the mobile device 104, can generate the diagnosis. In a third implementation, the patient-application 108 can communicate with a clinician-application 112 executed on a computing device 114 via the computing server 110. In that third implementation, a clinician can review the signal on the clinician-application 112 and can input a diagnosis on the clinician-application 112, which can then transmit the diagnosis to the patient-application 108 for display thereon.

The electrocardiography device 102 is described in further detail below by FIGS. 2-6. The electrocardiography device 102 can be used and may be recommended where the patient 106 has had or is at risk for: myocardial infarction (e.g., heart attack), chest pain, pulmonary embolism, shortness of breath, third heart sound, fourth heart sound, a cardiac murmur, a structural heart disease, cardiac dysrhythmias either by pulse or palpitations, a condition of fainting or collapsing, seizures, drug-induced QT prolongation, electrolyte abnormalities such as hyperkalemia, any form of anesthesia, and/or any cardiac, vascular or pulmonary health problem.

The mobile device 104 can be a mobile phone. Although a mobile phone is described, in alternate implementations, the mobile device 104 can be a tablet computer, a phablet computer, any other mobile device, or any combination thereof.

The patient 106 can be a cardiac patient who may frequently, quickly and/or conveniently need an electrocardiography to diagnose the information about the structure of the heart and the function of its electrical conduction system. The electrocardiography can measure the rate and rhythm of heartbeats of the patient 106, the size and position of the heart chambers of the patient 106, the presence of any damage to the muscle cells or conduction system of the heart of the patient 106, the effects of cardiac drugs on the heart of the patient 106, and/or the like.

The patient-application 108 can be a software application executed on the mobile device 104, which can have an iPhone operating system (IOS), ANDROID, or any other operating system.

The computing server 110 can be a device or a computer program that can provide functionality for the electrocardiography device 102 and/or the mobile device 104, which can be referred to as clients of the computing server 110. The computing server 110 can be a cloud computing server, as explained below by FIG. 9. In an alternate implementation, the computing server 110 can be a cluster of computers. In another implementation, the computing server 110 can be one or more of: a desktop computer, a laptop computer, a tablet computer, a phablet computer, a cellular/smart phone, and any other suitable computing device. The computing server 110 can be communicatively coupled with each of the electrocardiography device 102 and the mobile device 104 via a communication network, such as one or more of: local area network, internet, wide area network, metropolitan area network, BLUETOOTH network, infrared network, wired network, and any other communication network.

The clinician-application 112 can be a software application executed on the computing device 114, which can have an iPhone operating system (IOS), ANDROID, or any other operating system.

The computing device 114 can be one or more of: a desktop computer, a laptop computer, a tablet computer, a phablet computer, a cellular/smart phone, and any other suitable computing device.

Figure 2:
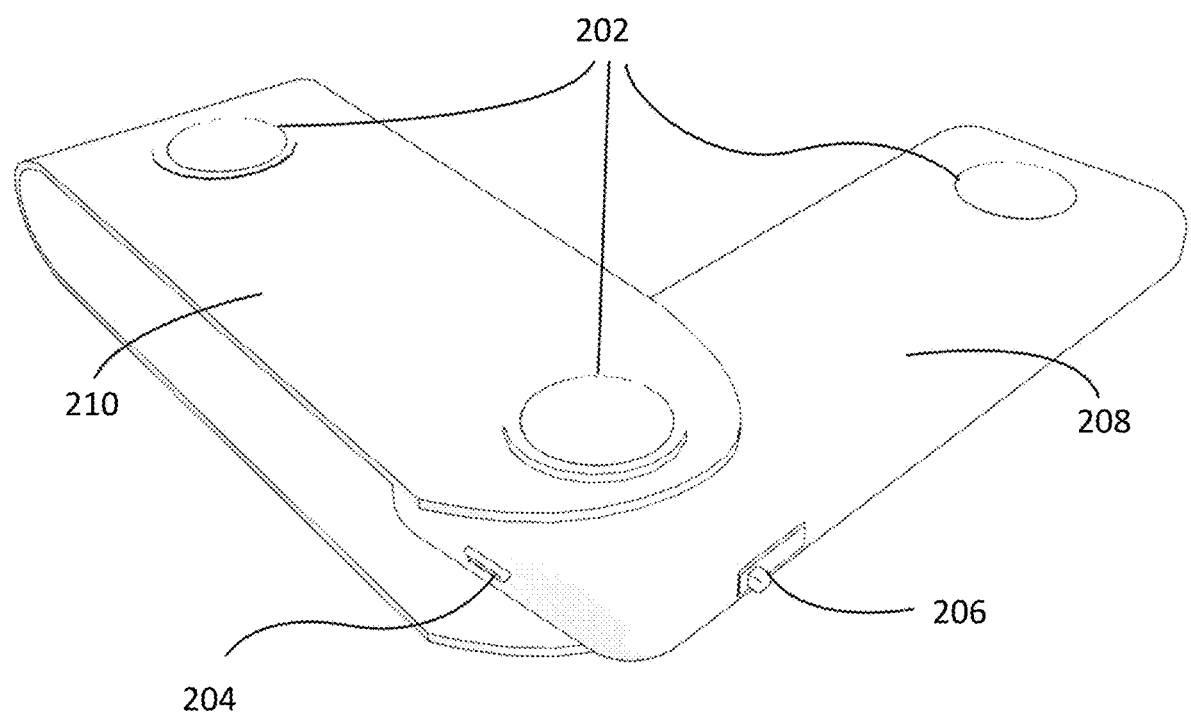
FIG. 2 illustrates the electrocardiography device in an open configuration.

FIG. 2 illustrates the electrocardiography device 102 in an open configuration. The electrocardiography device can include three electrodes 202, a charging port 204, a power switch 206, a main body 208 that can include a circuit board and rechargeable battery, and an adjustable cap 210 that can be moved to orient the electrodes 202 on suitable locations on the body of the patient 106.

The electrodes 202 can be unipolar electrodes or bipolar electrodes. The electrodes 202 can be plate electrodes. Although plate electrodes are described, in alternate implementations, the electrodes 202 can be suction electrodes, fluid column electrodes, flexible electrodes, any other type of electrode, and/or any combination thereof. The electrodes 202 can be made of silver or silver chloride because the electrode potential of these electrodes is stable when those electrodes 202 are exposed to biological tissue of the patient 106. In alternate implementations, the electrodes can be made of any other metal or alloy, such as nickel, German silver, stainless steel, and/or the like.

The electrodes 202 are configured to be placed closely or tightly with various points on the body of the patient 106 when the electrocardiography is being performed. Alternately or additionally, the electrodes 202 can be held onto the skin of the patient 106 by using an adhesive tape, which may look like a bandage. Such bandage-like electrodes can be beneficial when the patient is an infant or a toddler, and is unlikely to retain the electrodes on skin without the adhesive tape. Alternately or additionally, the electrodes 202 can include or be attached to a compressor, which can create a suction so as to generate a vacuum, which can cause the electrodes 202 to remain in place on the skin of the patient 106.

The electrodes 202 may not be connected with any conductors or leads. This can advantageously make the electrocardiography device 102 simple and convenient to use by the patient 106 and to move around. While the electrodes 202 are described as not having any conductors or leads, in an alternate implementation, the electrocardiography device 102 may have electronic points rather than electrodes 202 on the main body 208 and the adjustable cap 210, and those electronic points may be connected to the electrodes via conductors or leads.

The charging port 204 can be used to charge the rechargeable battery within the main body 208. The rechargeable battery can power the circuit board within the main body 208, including the components on that circuit board. The charging port can be a Universal Serial Bus (USB) Type-C port, USB Type-B port, USB Type-A port, microUSB port, USB 3.1 port, a LIGHTNING port, any other port, any combination thereof, and/or the like.

The power switch 206 can be configured to be turned on when the electrocardiography is being performed. When the power switch is turned on, the circuit board within the main body 208 can be activated. The power switch 206 may be turned off when the electrocardiography is not being performed.

The main body 208 can include the circuit board and the rechargeable battery, as noted above.

The adjustable cap 210 can be rotated around an axis perpendicular to the main body 208, as is clear from FIGS. 2-6. The rotation advantageously allows the electrodes 202 to be extended to different portions of the body of the patient 106.

Most or almost the entire surface area of the electrocardiography device 102 can be made of highly-durable plastic and silicone materials, which can protect the electrocardiography device 102 against water, shock, dust, dirt, grease, scratches, and drops. Some examples of such materials are polyurethane plastics, such as thermoplastic polyurethane.

While three electrodes 202 are described, in alternate implementations the electrocardiography device 102 can have any other number of electrodes, such as two, four, five, six, seven, eight, nine, ten, eleven, twelve, thirteen, or so on.

Figure 3:
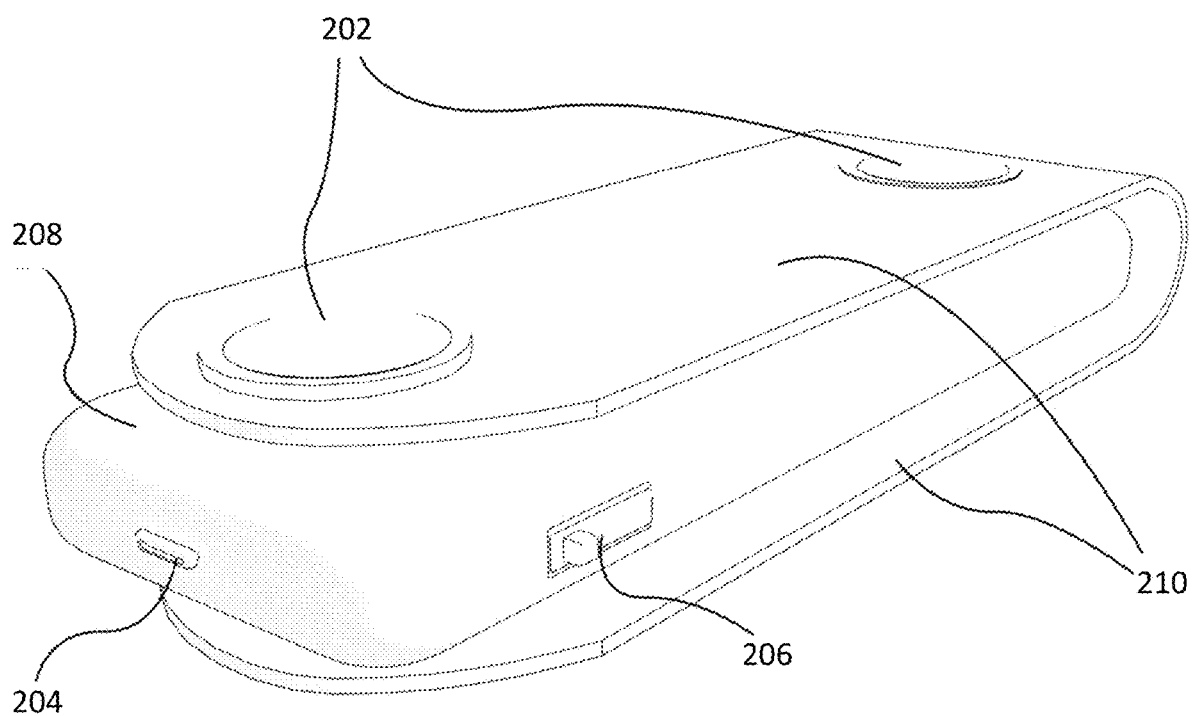
FIG. 3 illustrates a view the electrocardiography device in a closed configuration.

FIG. 3 illustrates the electrocardiography device 102 in a closed configuration.

Figure 4:
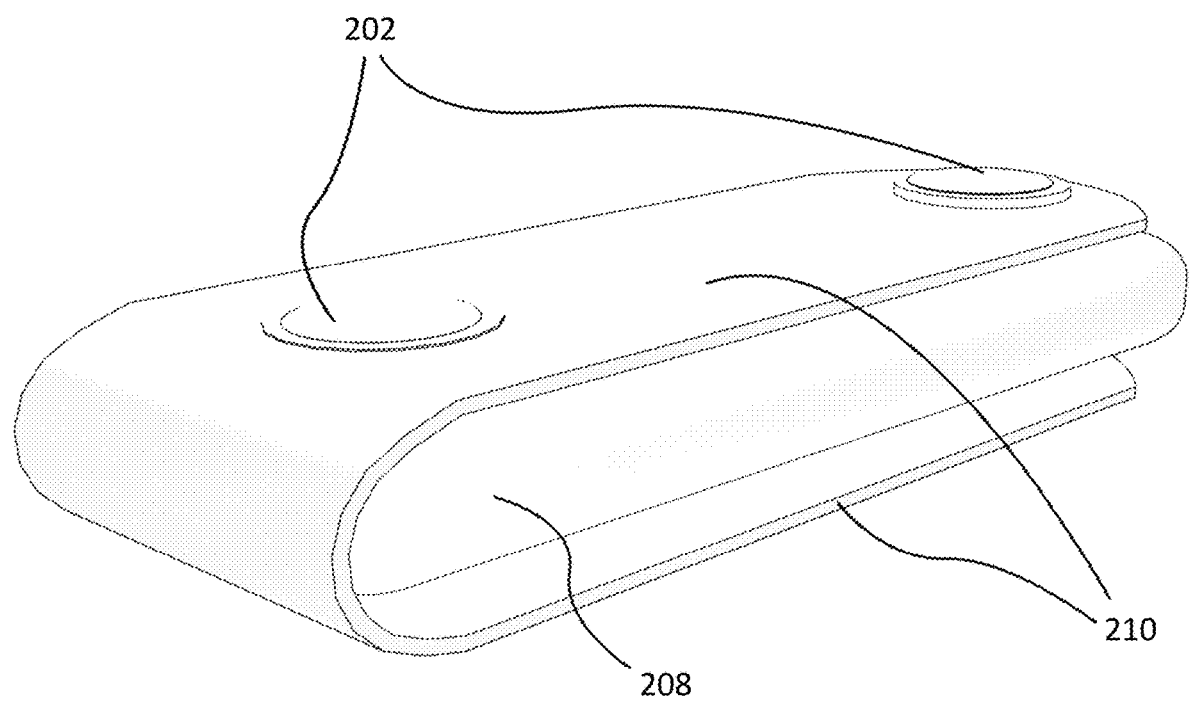
FIG. 4 illustrates another view of the electrocardiography device in the closed configuration.

FIG. 4 illustrates another view of the electrocardiography device 102 in the closed configuration.

Figure 5:
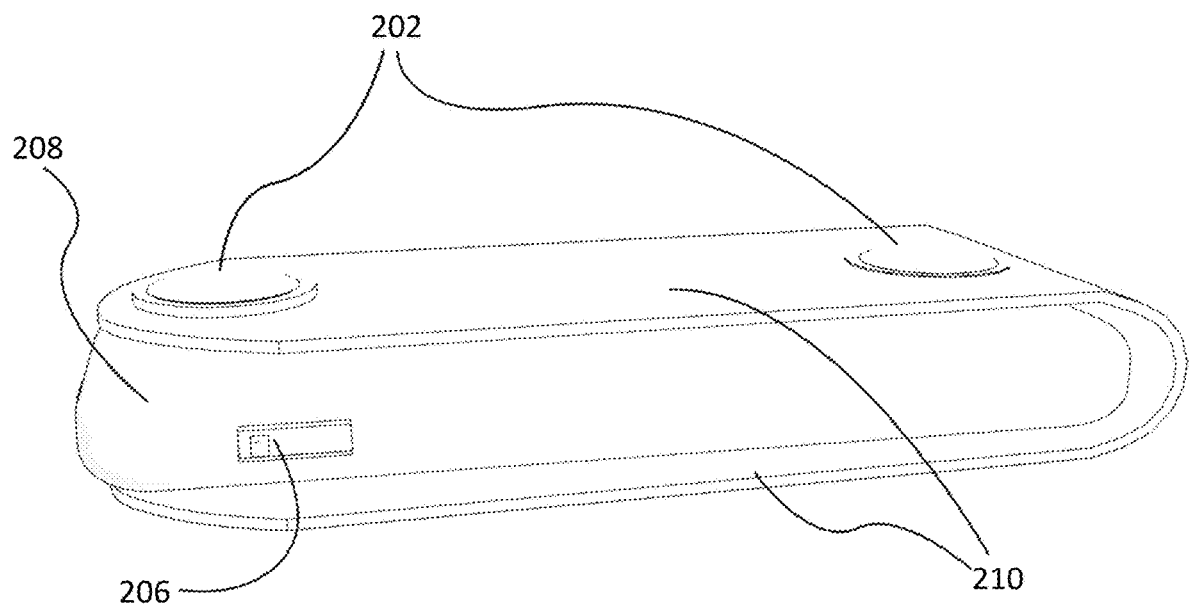
FIG. 5 illustrates another view of the electrocardiography device in the closed configuration.

FIG. 5 illustrates another view of the electrocardiography device 102 in the closed configuration.

Figure 6:
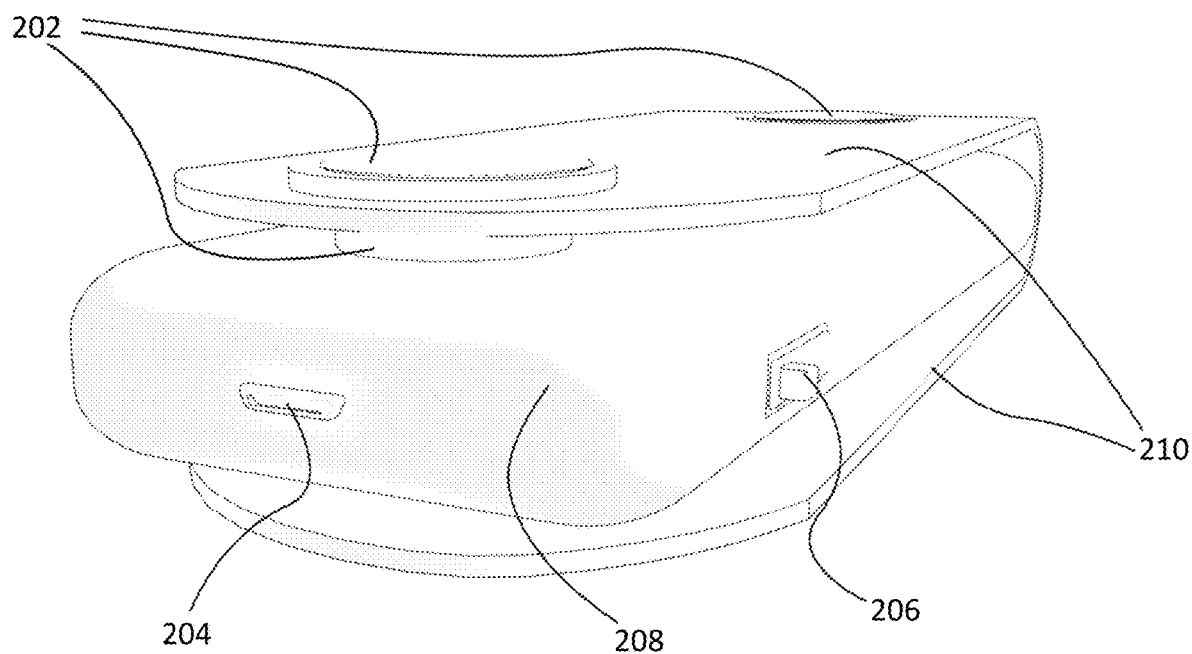
FIG. 6 illustrates another view of the electrocardiography device in the closed configuration.

FIG. 6 illustrates another view of the electrocardiography device 102 in the closed configuration.

Figure 7:
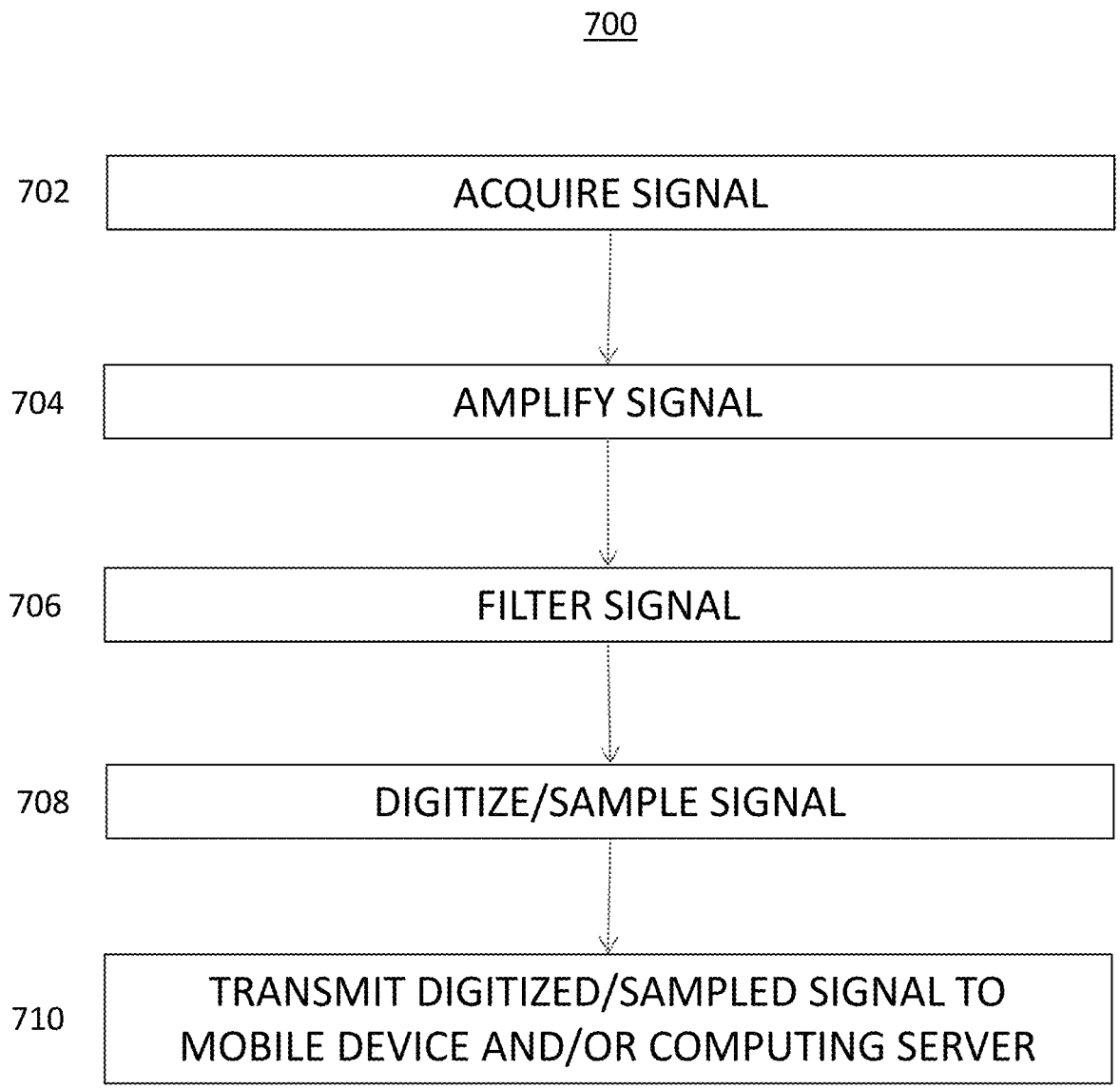
FIG. 7 illustrates a method, performed by the electrical circuit within the main body of the electrocardiography device, of acquiring a signal from the electrode, processing the signal so that it can be used by a mobile device and/or a computing server, and transmitting the processed signal to the mobile device and/or the computing server.

FIG. 7 illustrates a method 700, performed by the electrical circuit within the main body 208 of the electrocardiography device 102, of acquiring a signal from the electrode 202, processing the signal so that it can be used by a mobile device 104 and/or a computing server 110, and transmitting the processed signal to the mobile device 104 and/or the computing server 110. The electrical circuit within the main body 208 can include a communication receiver, one or more electronic amplifiers, one or more electronic filters, an analog to digital converter, and a communication transmitter, all of which may be communicatively coupled with each other.

The communication receiver can acquire, at 702, the signal from the electrodes 202. The acquired signal can have a voltage of less than 1 millivolt. The one or more electronic amplifiers, which are connected to the receiver, can amplify, at 704, the acquired signal. In one example, the one or more electronic amplifiers can include a pre-amplifier—which can amplify a very weak signal and provide the amplified signal to an instrumentation amplifier—and the instrumentation amplifier, which can be a type of a differential amplifier that has been outfitted with input buffer amplifiers, which can eliminate the need for input impedance matching. The amplification by the instrumentation amplifier can increase the signal amplitude for further processing.

The one or more electronic filters, which are connected to the one or more electronic amplifiers, can filter, at 706, the amplified signal. The one or more filters can be at least one notch filter, which is a band-stop filter with a narrow stopband. A band-stop filter can be a filter that passes most frequencies unaltered, but attenuates those in a specific range to very low levels. The notch filter can advantageously reduce amplifier peaking, increase gain flatness, reduce audio feedback (if any), and remove a band of unwanted frequencies while allowing other frequencies to pass with minimum loss.

The analog to digital converter, which is connected to the one or more electronic filters, can extract, at 708, samples—i.e., values at discrete points in time of the signal—from the continuous filtered signal. The sampled signal can also be referred to as digital signal. The communication transmitter, which is connected to the analog to digital converter, can transmit, at 710, the digitized or sampled signal to the mobile device 104 and/or the computing server 110.

While the one or more electronic amplifiers and the electronic filter are described as being a part of the electrical circuit within the main body 208, in alternate implementations at least one of these two components can be within the housing encompassing each electrode 202. In these alternate implementations, the electrical circuit within the main body 208 does not perform the amplification and the filtering of the signal.

Figure 8:
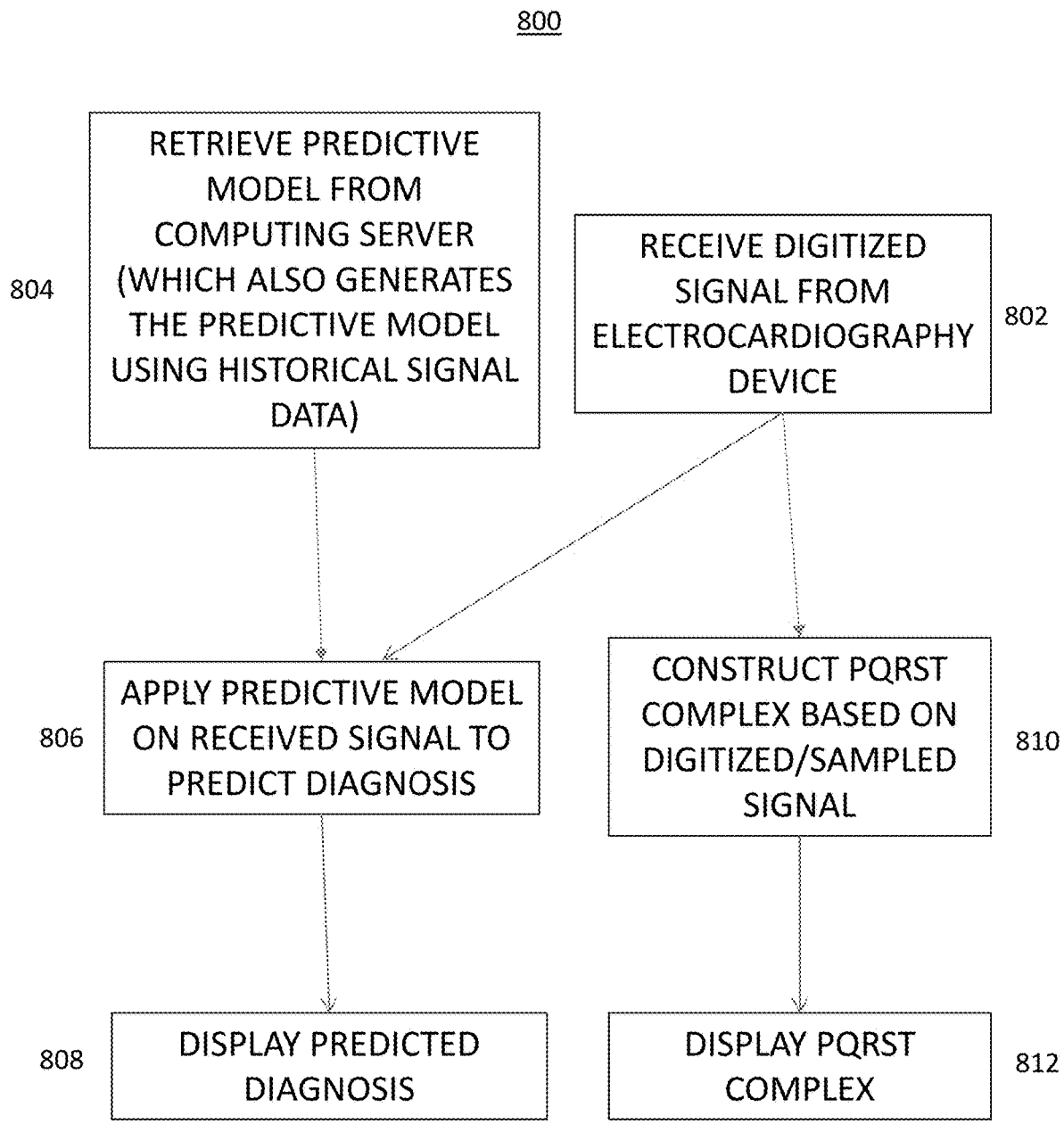
FIG. 8 illustrates a method, performed by at least one programmable processor of the mobile device, to analyze the received signal to predict a diagnosis based on the received signal and to construct a PQRST complex based on and specific to the signal, and then to display the predicted diagnosis and the PQRST complex in the patient-application.

FIG. 8 illustrates a method, performed by at least one programmable processor of the mobile device 104, to analyze the received signal to predict a diagnosis based on the received signal and to construct a PQRST complex based on and specific to the signal, and then to display the predicted diagnosis and the PQRST complex in the patient-application 108.

The at least one programmable processor can receive, at 802, a digitized/sampled signal of the patient 106 from the electrocardiography device 102 via a communication network, such as a BLUETOOTH network. Although a BLUETOOTH network is described, in alternate implementations, any other communication network can be used, such as one or more of: local area network, internet, wide area network, metropolitan area network, infrared network, wired network, and any other communication network.

The at least one programmable processor can retrieve, at 804, a predictive model from the computing server 110. The predictive model may have been generated earlier by the computing server 110 by using historical electrocardiograph-signal data of either the patient 106 alone or of multiple patients. The predictive model can be a regression based model or a machine-learning based model. The regression model can be one of: a linear regression model, a discrete choice model, a logistic regression, a multinomial logistic regression, a probit regression, a logit regression, a time-series model, a survival or duration model, a classification and regression tree (CART), multivariate adaptive regression splines, any other regression model, any combination thereof, and/or the like. The machine-learning based model can be: a neural network, a multilayer perceptron (MLP), a radial basis function, a support vector machine, a Naïve Bayes model, k-nearest neighbors model, a geospatial predictive model, any other machine-learning based model, any combination thereof, and/or the like.

The at least one programmable processor can apply, at 806, the predictive model on the signal received at 802 to predict the diagnosis of the patient 106. The at least one programmable processor can display, at 808, the predicted diagnosis on a graphical user interface of the patient-application 108.

The at least one programmable processor can construct, at 810, the PQRST wave/complex based on the digitized or sampled signal. The PQRST complex is described below.

The P wave within the PQRST complex can correspond to the atrial depolarization and the pumping of blood from the atrium to the ventricle. Any abnormal P wave (e.g., inverted, too high, too long, or missing P wave) can indicate atrial fibrillation.

Each QRS complex within the PQRST complex comes after a P wave for the atrium and ventricle to work synchronously. The QRS can correspond to the depolarization of blood and the pumping out of blood from the ventricle to the body and lung. There can be a short delay between the P wave and the QRS complex to allow time to fill the ventricle with blood and get ready to pump. If the delay is too long (e.g., more than 200 milliseconds), there may be a nodal block of electrical signal from the atrium to the ventricle. If the delay is too short (e.g., less than 120 milliseconds), the signal may find a shortcut to go from the SA node to the AV node. The distance between each QRS complex can correspond to the time for one heart beat. This distance can be stable between beats for a normal heart, but is not so in situations such as tachycardia, bradycardia, bigeminy, and a condition with a skipped heart beat.

The T wave within the PQRST complex can correspond to the repolarization of the ventricle and the recovery of the ventricle for the next cycle.

The at least one programmable processor can display, at 812, the constructed PQRST wave on a graphical user interface of the patient-application 108.

Figure 9:
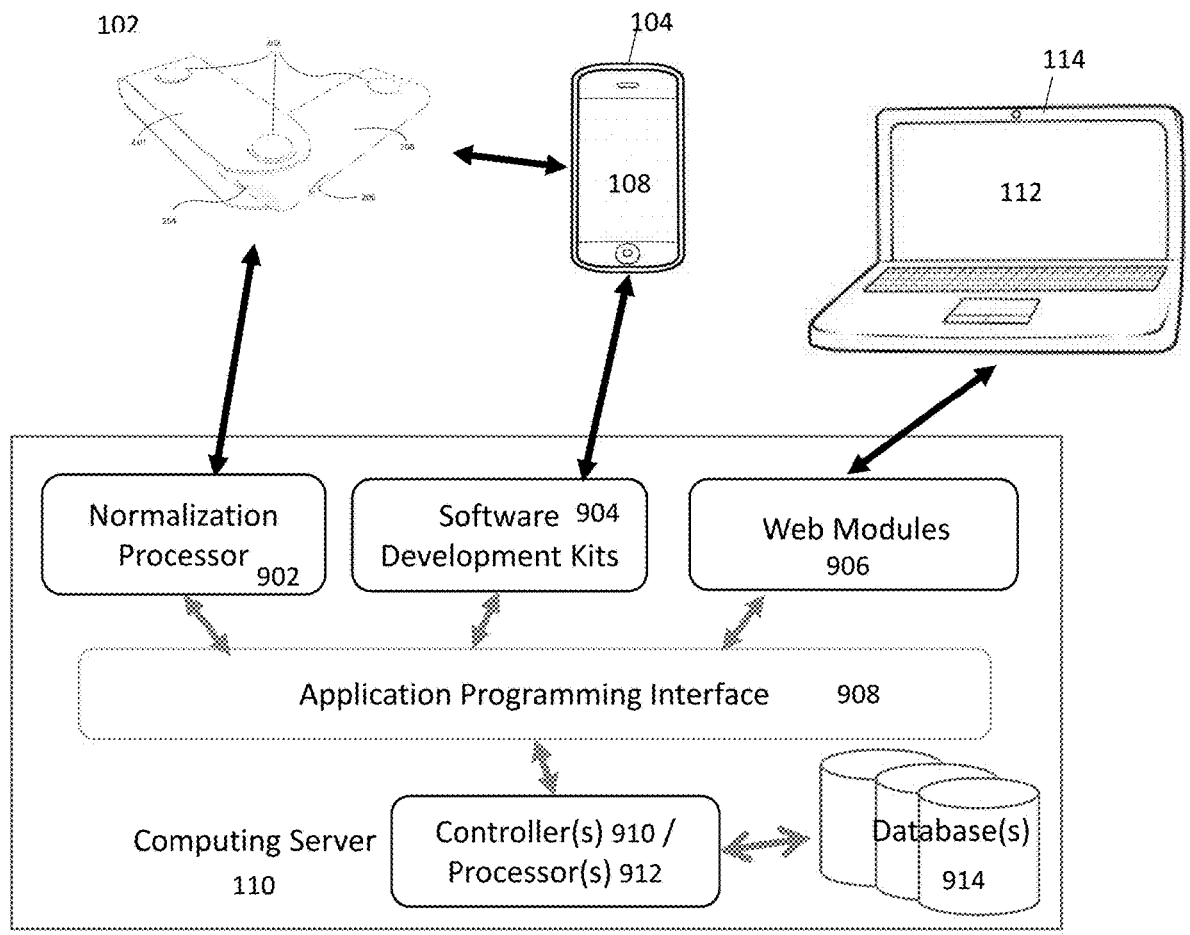
FIG. 9 illustrates one example of the computing server.

FIG. 9 illustrates one example of the computing server 110. The computing server 110 can be a cloud computing server. The cloud computing server 110 can include a normalization processor 902, one or more software development kits (SDKs) 904, one or more web modules 906, an application programming interface (API) 908, one or more controllers 910 including one or more processors 912, and one or more databases 914 connected to the one or more controllers 910.

The electrocardiography device 102 can receive a signal from the patient 106. The electrocardiography device 102 can amplify the acquired signal, and then filter the amplified signal. The electrocardiography device 102 can then digitize the continuous filtered signal by extracting samples—i.e., values at discrete points—from the continuous filtered signal. The electrocardiography device 102 can then transmit the digitized signal to the mobile device 104 and/or to the computing server 110.

The normalization processor 902 can be configured to communicate with the electrocardiography device 102 via a first communication network. The one or more SDKs 904 are configured to communicate, via a second communication network, with the mobile device 104 and the patient-application 108 executed thereon. The one or more web modules 906 can be configured to communicate, via a third communication network, with the computing device 114, and the clinician-application 112 executed thereon, when the computing device 114 is a laptop or a desktop computer. Each of the first communication network, the second communication network, and the third communication network can be one or more of: local area network, internet, wide area network, metropolitan area network, BLUETOOTH network, infrared network, wired network, and any other communication network. In one implementation, the first communication network, the second communication network, and the third communication network may be the same network. In another implementation, the first communication network, the second communication network, and the third communication network may be different networks. In the alternate implementation where the mobile device 104 is a laptop or a desktop computer, the mobile device 114 can communicate with the web modules 906. When the computing device 114 is a phone, a tablet computer or a phablet computer, the computing device 114 can communicate with the SDK 904 in that case.

The API 908 can be a set of subroutine definitions, protocols, and/or tools that define method of communication between the patient-application 108 and the computing server 110 and between the client-application 112 and the computing server 110. The API 908 can ensure, for example, that the data from the at least one of the normalization processor 902, the one or more SDKs 904, and the one or more web modules 906 can be read by the one or more controllers 910 and the one or more processors 912.

Each database 914 can be a cloud database, which can advantageously permit an easy scalability of the database 914 when required (e.g., when additional data needs to be stored, which can happen, for example, when the number of patients increase beyond a threshold value). In one implementation, access to that database 914 can be provided as a service. In some implementations, the database 914 can be run on virtual machine instances. In one implementation, the database 914 can be a disk storage. In some alternate implementations, the database 914 can be a main memory (e.g., random access memory) rather than a disk storage. In those alternate implementations, access of data from the main memory can advantageously eliminate seek time when querying the data, which can provides a faster access of data, as compared to accessing data from the disk.

The use of a cloud computing server 110 can be advantageous over a traditional server, as the cloud computing server 110 permits a quick scalability by addition of additional web services within in a few seconds. When the load on the patient-application 108 or clinician-application 112 increases, additional processors 912 or databases 914 can be added—or alternately the processing abilities of the existing processors 912 or databases 914 can be enhanced—within a few seconds. Additionally, inclusion of all of the normalization processor 902, one or more SDKs 904, one or more web modules 906, API 908, at least one data processor 912, and database 914 within the cloud computing server 110 can advantageously enable: a dynamic provisioning, monitoring and managing of the patient-application 108 and clinician-application 112; as well as a quick (e.g., within a few seconds) and easy restoring the patient-application 108 and/or the clinician-application 112 to a previous version of those applications if and when required.

Various implementations of the subject matter described herein can be realized/implemented in digital electronic circuitry, integrated circuitry, specially designed application specific integrated circuits (ASICs), computer hardware, firmware, software, and/or combinations thereof. These various implementations can be implemented in one or more computer programs. These computer programs can be executable and/or interpreted on a programmable system. The programmable system can include at least one programmable processor, which can have a special purpose or a general purpose. The at least one programmable processor can be coupled to a storage system, at least one input device, and at least one output device. The at least one programmable processor can receive data and instructions from, and can transmit data and instructions to, the storage system, the at least one input device, and the at least one output device.

These computer programs (also known as programs, software, software applications or code) can include machine instructions for a programmable processor, and can be implemented in a high-level procedural and/or object-oriented programming language, and/or in assembly/machine language. As can be used herein, the term "machine-readable medium" can refer to any computer program product, apparatus and/or device (for example, magnetic discs, optical disks, memory, programmable logic devices (PLDs)) used to provide machine instructions and/or data to a programmable processor, including a machine-readable medium that can receive machine instructions as a machine-readable signal. The term "machine-readable signal" can refer to any signal used to provide machine instructions and/or data to a programmable processor.

To provide for interaction with a user, the subject matter described herein can be implemented on a computer that can display data to one or more users on a display device, such as a cathode ray tube (CRT) device, a liquid crystal display (LCD) monitor, a light emitting diode (LED) monitor, or any other display device. The computer can receive data from the one or more users via a keyboard, a mouse, a trackball, a joystick, or any other input device. To provide for interaction with the user, other devices can also be provided, such as devices operating based on user feedback, which can include sensory feedback, such as visual feedback, auditory feedback, tactile feedback, and any other feedback. The input from the user can be received in any form, such as acoustic input, speech input, tactile input, or any other input.

The subject matter described herein can be implemented in a computing system that can include at least one of a back-end component, a middleware component, a front-end component, and one or more combinations thereof. The back-end component can be a data server. The middleware component can be an application server. The front-end component can be a client computer having a graphical user interface or a web browser, through which a user can interact with an implementation of the subject matter described herein. The components of the system can be interconnected by any form or medium of digital data communication, such as a communication network. Examples of communication networks can include a local area network, a wide area network, internet, intranet, BLUETOOTH network, infrared network, or other networks.

Although a few variations have been described in detail above, other modifications can be possible. For example, the logic flows depicted in the accompanying figures and described herein do not require the particular order shown, or sequential order, to achieve desirable results. Additional implementations may be within the scope of the following claims.

What is claimed is:

1. An electrocardiography device comprising:
   a main body including an electrode of a plurality of electrodes, wherein the plurality of electrodes are configured to acquire an electrical signal from a patient, the electrode of the plurality of electrodes being fixed on the main body;
   an adjustable cap including two electrodes of the plurality of three electrodes, the adjustable cap rotatable around an axis on the main body to orient the plurality of electrodes on different locations on a body of the patient, wherein the electrode in the main body is configured to be outside of the adjustable cap when the electrocardiography device is in an open configuration, and the electrode in the main body is configured to be within the adjustable cap when the electrocardiography device is in a closed configuration; and
   a power switch to activate the plurality of electrodes to acquire the electrical signal from the patient.

2. The electrocardiography device of claim 1, wherein the main body further includes an electrical circuit and a rechargeable battery.

3. The electrocardiography device of claim 2, wherein the electrical circuit comprises:
   a communication receiver configured to receive the acquired electrical signal from the plurality of electrodes;
   one or more electronic amplifiers configured to amplify the received electrical signal;
   one or more electronic filters configured to filter the amplified electrical signal;
   an analog to digital converter configured to extract samples at discrete points in time of the filtered electrical signal; and
   a transmitter configured to transmit the samples to a mobile device.

4. The electrocardiography device of claim 3, wherein the one or more electronic amplifiers include a pre-amplifier and an instrumentation amplifier.

5. The electrocardiography device of claim 3, wherein the one or more electronic filters include a notch filter.

6. The electrocardiography device of claim 2, wherein the rechargeable battery is configured to power the electrical circuit, wherein the electrocardiography device further comprises a charging port, configured to charge the rechargeable battery.

7. The electrocardiography device of claim 1, wherein the plurality of electrodes are made of one of silver and silver chloride.

8. The electrocardiography device of claim 1, wherein the plurality of electrodes are leadless.

9. The electrocardiography device of claim 1, wherein the main body is made of thermoplastic polyurethane.

10. The electrocardiography device of claim 1, wherein the main body is placed within the adjustable cap when the electrocardiography device is in the closed configuration.

11. The electrocardiography device of claim 1, wherein the main body is substantially tangential to the adjustable cap when the electrocardiography device is in the open configuration, and the main body is substantially parallel to the adjustable cap when the electrocardiography device is in the open configuration.

12. The electrocardiography device of claim 1, wherein at least one electrode is attached to a compressor, configured to create a suction so as to generate a vacuum.

13. A system comprising:
an electrocardiography device configured to receive an electrical signal from a body of a patient, and process the electrical signal to extract samples at discrete points in time of the electrical signal to generate a sampled signal, wherein the electrocardiography device comprises:
a main body including an electrode of a plurality of electrodes, configured to acquire the electrical signal from the body of the patient, the electrode of the plurality of electrodes being fixed on the main body; and
an adjustable cap including two electrodes of the plurality of electrodes, the adjustable cap rotatable around an axis on the main body to orient the plurality of electrodes on different locations on the body of the patient, wherein the electrode in the main body is configured to be outside of the adjustable cap when the electrocardiography device is in an open configuration, and the electrode in the main body is configured to be within the adjustable cap when the electrocardiography device is in a closed configuration; and
a mobile device configured to:
receive, via a first communication network, the sampled signal from the electrocardiography device;
retrieve, via a second communication network, a predictive model from a computing server;
apply the predictive model on the sampled signal to predict a diagnosis for the patient; and
display the diagnosis on a first graphical user interface.

14. The system of claim 13, wherein the mobile device is further configured to:
construct a PQRST complex based on the sampled signal; and
display the PQRST complex on a second graphical user interface of the mobile device.

15. The system of claim 13, wherein the computing server is a cloud computing server.

16. The system of claim 15, wherein the cloud computing server comprises:
a normalization processor configured to receive the sampled signal from the electrocardiography device;
at least one of one or more software development kits and one or more web modules configured to facilitate communication with the mobile device;
an application programming interface configured to facilitate communication between one or more processors and the mobile device;
one or more controllers including the one or more processors; and
one or more databases communicatively coupled to the one or more controllers.

17. A method comprising:
generating, using a plurality of electrodes of an electrocardiography device, a vacuum between the plurality of electrodes and a patient;
acquiring, by the plurality of electrodes of the electrocardiography device, an electrical signal from a patient;
receiving, by a communication receiver of the electrocardiography device, the acquired electrical signal from the plurality of electrodes;
amplifying, by one or more electronic amplifiers within the electrocardiography device, the received electrical signal; filtering, by one or more electronic filters of the electrocardiography device, the amplified electrical signal;
extracting, by an analog to digital converter of the electrocardiography device, samples at discrete points in time of the filtered electrical signal; and
transmitting, by a transmitter of the electrocardiography device, the samples to a mobile device.

18. The method of claim 17, wherein the electrocardiography device includes an adjustable cap including two electrodes of the plurality of electrodes, the adjustable cap being rotated around an axis on a main body to orient the plurality of electrodes on different locations on a body of the patient.

19. The method of claim 17, wherein the electrocardiography device includes a power switch, the power switch activating the plurality of electrodes to acquire the electrical signal from the patient.

20. The method of claim 17, wherein the mobile device performs operations comprising:
receiving, via a first communication network, the samples from the electrocardiography device;
retrieving, via a second communication network, a predictive model from a computing server, wherein the predictive model is one of a neural network, a multilayer perceptron (MLP), a radial basis function, a support vector machine, a Naïve Bayes model, k-nearest neighbors model, or a geospatial predictive mode;
applying the predictive model on the samples to predict a diagnosis for the patient; and
displaying the diagnosis on a first graphical user interface of the mobile device.

* * * * *